(12) United States Patent
Collins et al.

(10) Patent No.: US 8,690,883 B2
(45) Date of Patent: Apr. 8, 2014

(54) ARTICULATING INJECTION CANNULA AND SEAL ASSEMBLY

(75) Inventors: Keith Collins, Milford, CT (US); Thomas G. Wilson, Guilford, CT (US); Spanky A. Raymond, Uniontown, OH (US)

(73) Assignee: Spine Wave, Inc., Shelton, CT (US)

( * ) Notice: Subject to any disclaimer, the term of this patent is extended or adjusted under 35 U.S.C. 154(b) by 1397 days.

(21) Appl. No.: 11/969,303

(22) Filed: Jan. 4, 2008

(65) Prior Publication Data
US 2008/0172060 A1   Jul. 17, 2008

Related U.S. Application Data

(63) Continuation-in-part of application No. 11/170,010, filed on Jun. 29, 2005, now Pat. No. 7,722,579, and a continuation-in-part of application No. 11/170,577, filed on Jun. 29, 2005, now Pat. No. 7,789,913, and a continuation-in-part of application No. 11/170,382, filed on Jun. 29, 2005, now Pat. No. 7,556,650, and a continuation-in-part of application No. 11/169,405, filed on Jun. 29, 2005, now Pat. No. 7,740,660, and a continuation-in-part of application No. 11/170,588, filed on Jun. 29, 2005, now Pat. No. 7,837,733, and a continuation-in-part of application No. 11/170,657, filed on Jun. 29, 2005, now Pat. No. 8,337,557.

(60) Provisional application No. 60/883,472, filed on Jan. 4, 2007, provisional application No. 60/683,665, filed on Jun. 29, 2004, provisional application No. 60/843,256, filed on Sep. 28, 2006.

(51) Int. Cl.
*A61B 17/58* (2006.01)
*A61B 17/60* (2006.01)
*A61F 2/00* (2006.01)
*A61M 5/178* (2006.01)
*A61M 5/00* (2006.01)

(52) U.S. Cl.
USPC .......... 606/94; 606/93; 604/165.01; 604/239

(58) Field of Classification Search
USPC ............ 606/94, 93; 604/167.03, 165.04, 239, 604/278, 165.01; 128/888; 600/208; 623/23.68
See application file for complete search history.

(56) References Cited

U.S. PATENT DOCUMENTS 1,695,263 A * 12/1928 Jacques ........................ 138/120
1,705,443 A *  3/1929 Edelmann ................ 285/148.15

(Continued)

OTHER PUBLICATIONS

PCT Search and Opinion for PCT/US08/50251 (related international application), May 22, 2008, pp. 3, 6-8.

*Primary Examiner* — Michael T Schaper
*Assistant Examiner* — David Bates
(74) *Attorney, Agent, or Firm* — Hoffmann & Baron, LLP (57) ABSTRACT

An assembly for sealably injecting a fluent material into an intradiscal space accessed through an opening in the annulus of a spinal disc comprises a cannula having a passageway for injecting the fluent material therethrough into the intradiscal space, a seal having a sealing surface for sealing engagement with the outer surface of the disc annulus and defining a central opening for, and an articulating joint defined between the central opening of the seal and the cannula configured to permit relative articulation between the components. The assembly may further comprise an anchor element extending through the central opening of the seal, the anchor element including an elongated threaded body sized for threaded engagement within the opening in the disc annulus and having a head configured to engage a distal end of the cannula.

11 Claims, 8 Drawing Sheets

(56) References Cited

U.S. PATENT DOCUMENTS

| | | | |
|---|---|---|---|
| 4,462,394 A * | 7/1984 | Jacobs | 606/94 |
| 4,815,454 A * | 3/1989 | Dozier, Jr. | 606/94 |
| 5,405,330 A * | 4/1995 | Zunitch et al. | 604/240 |
| 5,520,678 A * | 5/1996 | Heckele et al. | 606/1 |
| 5,741,265 A * | 4/1998 | Chan | 606/94 |
| 6,018,094 A * | 1/2000 | Fox | 606/191 |
| 6,217,581 B1 * | 4/2001 | Tolson | 606/86 R |
| 6,267,770 B1 * | 7/2001 | Truwit | 606/130 |
| 6,517,519 B1 * | 2/2003 | Rosen et al. | 604/164.06 |
| 6,527,782 B2 * | 3/2003 | Hogg et al. | 606/130 |
| 6,592,573 B2 * | 7/2003 | Castaneda et al. | 606/1 |
| 6,802,822 B1 * | 10/2004 | Dodge | 604/82 |
| 6,979,336 B2 * | 12/2005 | Durniak | 606/92 |
| 7,112,205 B2 * | 9/2006 | Carrison | 606/92 |
| 8,460,305 B2 * | 6/2013 | Jordan et al. | 606/92 |
| 2002/0147496 A1 * | 10/2002 | Belef et al. | 623/17.12 |
| 2003/0083642 A1 * | 5/2003 | Boyd et al. | 604/506 |
| 2004/0092810 A1 * | 5/2004 | Daum et al. | 600/411 |
| 2004/0199192 A1 * | 10/2004 | Akahoshi | 606/169 |
| 2004/0225292 A1 * | 11/2004 | Sasso et al. | 606/73 |
| 2005/0143737 A1 | 6/2005 | Pafford et al. | |
| 2006/0004458 A1 | 1/2006 | Collins et al. | |
| 2006/0259006 A1 | 11/2006 | McKay et al. | |
| 2006/0293663 A1 | 12/2006 | Walkenhorst et al. | |

* cited by examiner

ARTICULATING INJECTION CANNULA AND SEAL ASSEMBLY

RELATED APPLICATIONS

This application claims priority to provisional application No. 60/883,472, which was filed on Jan. 4, 2007, and is a continuation-in-part of each of applications Ser. No. 11/170,010 now U.S. Pat. No. 7,722,579; Ser. No. 11/170,577 now U.S. Pat. No. 7,789,913; Ser. No. 11/170,382 now U.S. Pat. No. 7,556,650; Ser. No. 11/169,405 now U.S. Pat. No. 7,740,660; Ser. No. 11/170,588 now U.S. Pat. No. 7,837,733 and Ser. No. 11/170,657 now U.S. Pat. No. 8,337,557, all filed on Jun. 29, 2005, all of which claim priority to provisional application No. 60/683,665, filed on Jun. 29, 2004, as well as to provisional application No. 60/843,256, filed on Sep. 28, 2006. The disclosure of each of these applications is incorporated herein by reference.

BACKGROUND OF THE INVENTION

The present invention relates to systems and methods for the treatment of the spine, and especially the interbody disc space. More specifically, the invention concerns the injection of a biomaterial into a spinal space, such as the intradiscal space.

Spine fusion procedures represent the state of the art treatment for intervertebral disc problems, which generally involve open surgery and the use of interbody fusion cages and spinal fixation systems to stabilize the fusion site. An alternative treatment under evaluation is to replace or augment the disc or nucleus pulposus with a prosthetic device. Examples of some devices currently under investigation include in-situ cured polymers such as polyurethanes and protein polymers, which may have properties varying from a rubbery hydrogel to a rigid plastic. Problems associated with these devices occur during insertion, whereby the pressure required to fill the disc space can cause leakage of the material into sensitive adjacent areas.

A number of devices are available for distracting vertebral bodies or for injecting material into the disc. Some devices are capable of both distraction and injection using the same instrument. These types of devices typically use a deflated balloon attached to a cannula and inserted between the vertebral bodies. The balloon is inflated with a prosthetic fluid through the cannula to distract the vertebral bodies. This approach requires high-pressure delivery of the fluid to achieve the pressure needed to distract the vertebral bodies and to allow the balloon and fluid to permanently remain in the disc space. Alternatively, a separate device is used to inject the prosthetic fluid around the balloon and the balloon is used strictly for distraction after which it is deflated and removed.

Much of the prior art devices and methods contemplate free injection of biomaterial into a spinal space which may lead to uncontrolled leakage. The art also describes injection of the material into a deflated balloon, which requires leaving the balloon inside the disc space. Lastly, some methods require insertion under high pressure, thereby creating a potential for the prosthetic fluid to ooze or seep out of the disc space intra-operatively.

There is therefore a need for a system and method for introducing a biomaterial into a spinal space that is not prone to the problems of the prior art, especially the leakage problem experienced by the high pressure injection systems. This need extends to systems that can be easily utilized in a minimally invasive procedure.

SUMMARY OF THE INVENTION

In one aspect of the invention, an assembly is provided for sealably injecting a fluent material into an intradiscal space accessed through an opening in the annulus of a spinal disc. The assembly comprises a cannula having a passageway for injecting the fluent material therethrough into the intradiscal space, a seal having a sealing surface for sealing engagement with the outer surface of the disc annulus and defining a central opening, and an articulating joint defined between the central opening of the seal and the cannula configured to permit relative articulation therebetween. In certain embodiments, the articulating joint is a ball and socket joint to permit spherical articulation of the cannula relative to the seal, and therefore relative to the disc annulus. This articulation capability allows the surgeon to optimally position the cannula for injecting the fluent material while the seal is engaged to the annulus.

In one aspect, the central opening of the seal is sized for passage of the cannula therethrough and the cannula is sized so that its distal end extends through the central opening and through the opening in the annulus, while the proximal end is accessible outside the patient to mate with a source of the fluent material. In this embodiment, the socket is a generally spherical cavity defined in the seal while the ball is a generally spherical ball that defines a bore sized to receive the cannula therethrough. The cavity may be formed in a collar of the seal, along with a lip at the opening of the cavity that serves to retain the ball within the cavity.

In another feature, the assembly further comprises an anchor element extending through the central opening of the seal. The anchor element includes an elongated body sized for sealing engagement within the opening in the disc annulus and defining a bore for injecting the fluent material therethrough into the intradiscal space. The anchor element thus anchors the seal against the annulus as the fluent material is introduced through the cannula. The anchor element may define an annular recess at a proximal end thereof, while the central opening in the seal is sized to fit within the annular recess. In certain embodiments, the elongated body of the anchor element is threaded so that the anchor element may be threaded into the opening in the disc annulus. In these embodiments, the central opening of the seal is configured to permit relative rotation between the anchor element and the seal when the seal is engaged within the annular recess. The seal may also be sized to permit some axial play within the annular recess. With this feature, as the anchor element is threaded into the annulus, the anchor element will exert pressure against the seal to not only seal the central opening but also to enhance the sealing engagement of the sealing surface to the surface of the annulus.

In yet another aspect, the anchor element may include a head defined at a proximal end of the elongated body, in which the head is configured to engage a distal end of the cannula. In this embodiment, the cannula does not extend directly into the disc space, but rather engages the anchor element which provides the passageway for the fluid to flow from the cannula into the disc space. Thus, the cannula is sized so that a proximal end thereof is accessible outside the patient's body when the distal end is engaged to the anchor element. In this embodiment, the articulating joint is established at the interface between the anchor element and the distal end of the cannula. This articulating joint may again be a ball and socket engagement.

In a further aspect of the invention, an assembly for sealably injecting a fluent material into an intradiscal space accessed through an opening in the annulus of a spinal disc comprises a cannula sized to extend through the opening in the annulus of the spinal disc and having a passageway for injecting the fluent material therethrough into the intradiscal space, and a seal defining a bore for receiving the cannula therethrough and having a conical body defining external threads configured to engage the opening in the annulus. In this embodiment, the seal is configured to anchor itself to the disc annulus while providing a passageway for the introduction of the fluent material into the disc space.

Certain embodiments of the present invention thus provides an assembly for sealably injecting a fluent material into an intradiscal space that permits relative angulation between an introducer cannula and the disc annulus. Other embodiments provide an assembly for sealably injecting the fluent material in which a seal is anchored to the disc annulus. In yet other embodiments, the articulation and anchoring features are combined into an assembly that ensures fluid-tight introduction of a fluent material into a disc space.

DESCRIPTION OF THE PREFERRED EMBODIMENTS

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

In a particular procedure that may incorporate the present invention, an injectable nucleus is surgically introduced into the spine as a replacement for or augment to the natural nucleus pulposus. The injectable nucleus is preferably a curable biocompatible polymer with properties that emulate those of the natural human disc. A suitable injectable nucleus material is disclosed in U.S. Pat. Nos. 6,423,333; 6,033,654; and 5,817,303, which issued to Protein Polymer Technologies, Inc. The disclosures or these patents are incorporated herein by reference. These patents disclose a proteinaceous curable polymer that has physical properties close to those of the human disc nucleus pulposus and that includes certain adhesive properties that allow the polymer to adhere to the disc annulus and any remaining disc nucleus pulposus. It is of course understood that this material is illustrative for the purposes of the present disclosure and that other injectable materials are contemplated.

In a first step of the technique, the constituents of the injectable nucleus material are prepared in a mixing system, such as the mixing system disclosed in co-pending, commonly assigned patent application Ser. No. 10/803,214, entitled "Systems and Methods for Mixing Fluids", the disclosure of which is incorporated herein by reference. The mixing system is placed on the sterile table until it is needed for the mixing and injection step.

Where the biomaterial is an injectable nucleus, access to the intradiscal space is required. While many surgical approaches may be used, in one specific embodiment, the surgeon will use an extraforaminal mini-open approach to the disc. This may be either by a lateral retroperitoneal approach or a paramedian approach through the paraspinal muscles of the back. Access to the nucleus is gained through an extraforaminal annulotomy, so as to not expose the spinal canal or foramen to any undue risk. The annulus is identified and a minimal annulotomy is performed to gain access to the intradiscal space. The nucleus pulposus is then partially or completely removed using known techniques, such as using pituitary rongeurs and/or curettes. The nucleotomy should be fully irrigated once all loose fragments have been manually removed.

Once a predetermined amount of disc nucleus is removed, the size of the space may be verified, such as by visualization and/or use of a saline injected balloon. When the disc space is ready to receive the injectable nucleus, the disc space may be distracted using several techniques. In one technique, distraction of the disc is accomplished using a non-compliant inflatable spherical balloon, such as a 15 mm diameter spherical balloon.

Once the desired amount of distraction has been obtained, the distraction tool, such as the spherical balloon, may be removed from the disc. At this point, a trial balloon may be used again to estimate the volume of injectable nucleus needed to the fill the distracted space.

With the disc space maintained in distraction (whether by physical positioning of the patient or by separate instrumentation), the injectable nucleus may be mixed and injected into the disc space. Thus, an injection cannula may be provided as part of an injection assembly, such as the assembly 40 shown in FIG. 1. Details of the injection assembly 40 may be gleaned from previously incorporated co-pending application Ser. No. 11/170,010, and particularly the description associated with FIGS. 13-16 thereof, the disclosure of which is incorporated herein by reference. The injection cannula 42 extends through a seal element 46 that is configured to provide an essentially fluid tight seal against the disc annulus A. A vent 44 also extends through the seal 46. In a particular form of the construction, the seal 46 includes a body 48, as shown in FIG. 2, which is formed of a resilient material that can be compressed slightly under manual pressure to conform to the irregular external surface of the disc. The body 48 defines a sealing face 50 that bears against the disc annulus A (FIG. 1) to create a fluid tight seal.

Extending from the sealing face 50 is an engagement boss 52. The boss 52 in this arrangement is configured in accordance with the shape of the annulotomy cut into the annulus. As illustrated in FIG. 2, the boss 52 is also cruciate in shape with wings 53 that are sized to fit within corresponding legs of a cruciate cut into the annulus A. The leading edges 53a of the wings 53 can be rounded to facilitate placement of the boss 52 within the annulotomy. The vent 44 provides an additional wing 57 having a channel 58 that integrates with the hollow vent 44.

In accordance with another aspect of the procedure, the cannula is introduced through the annulotomy, while carefully retracting the nerve root, until the plug seal 50 seats against the annulus. Pressure is applied to the seal 46 to ensure that no injectable nucleus leaks out between the seal and annulus. Preferably, this pressure is applied manually by the surgeon by simply pressing the needle or cannula 42 toward the annulus. Since the injectable nucleus injection occurs at low pressures, the amount of force required to maintain a fluid-tight seal between the seal face 50 and the annulus is minimal.

The injectable nucleus is injected into the space until injectable nucleus is seen flowing through or out of the vent tube. At this point, the injection is stopped and the cannula is held in place until the injectable nucleus takes its initial set. A microscope or loupe may be used to visualize the injection process. The injectable nucleus is preferably allowed to substantially completely cure before the injection cannula assembly 40 is removed and the surgical site is closed. The cure period depends upon the particular injectable nucleus material. For the specific proteinaceous polymer discussed above, the cure period is a minimum of about five minutes.

The seal 46 is formed of a resilient and deformable material so that it can be compressed against the annulus A to form a fluid tight seal. For instance, the seal 40 may be formed of SILASTIC® or a similar elastomeric material.

The procedures described heretofore are particularly well suited for open surgical procedures where a microdiscectomy is performed to remove all or a portion of the disc nucleus. One such procedure is for the treatment of degenerative disc disease (DDD) where a total or partial nucleotomy is indicated. In such an open procedure access to the spinal disc is accomplished through an incision made through the skin and subcutaneous body tissue down to the surgical site is displaced and retracted. In the case of DDD, the annulus is typically relatively intact so that only a minimal annulotomy is necessary to gain access to the intradiscal space. It is preferred that the opening be as small as feasible to minimize damage to the annulus. In one embodiment, access can be via a K-wire over which a dilator, or a series of dilators, is passed. However, the nucleus pulposus may be significantly underhydrated or may contain fissures throughout the nucleus material, producing patient pain and giving rise to the need for a total or substantially total discectomy.

In such a DDD procedure, in addition to the steps described above, the surgeon may also choose to perform an intraoperative step of determining the integrity of the annulus, to confirm that the annulus is competent to withstand the distraction and injectable nucleus injection pressures. To accomplish this test, upon completion of the partial or total nucleotomy and creation of an intradiscal space within the disc annulus, a saline solution may be injected into the intradiscal space through the annulotomy opening. A saline solution is preferred since it is relatively easy to aspirate for removal from the intradiscal space. However, other suitable solutions may also be used. The saline solution may be injected through a vented cannula, in design and construction similar to the cannula assembly 40 shown in FIGS. 1-2. When the saline injection is under relatively low pressure (on the order of 25-40 psi under thumb pressure from the syringe and pressing the seal 46 against the external surface of the annulus), this step evaluates the integrity of the disc annulus—i.e., detects whether fissures or rents may be present in the annulus. This detection may be by tactile feel and/or by observation of leakage only at the injection cannula site.

Alternatively, or additionally, the injected saline solution may be used to determine the volume of the disc space to be filled with injectable nucleus material. If preferred, a trial balloon may be used to ascertain the volume of the intradiscal space to be filled. After the annulus integrity and volume tests have been completed, suction is applied to aspirate the nuclear cavity and a surgical swab may be used to wick away excess moisture that may interfere with the injection of the injectable nucleus material. Thereafter, the surgeon may use a distraction balloon to apply a distraction force within the intradiscal space to distract the opposing vertebral bodies on either side of the intradiscal space, further separating apart such vertebral bodies. A subsequent saline test may be conducted to further verify the integrity of the annulus. The injectable nucleus may then be sealably injected under pressure using the vented cannula assembly 40 as described hereinabove. Such injection of injectable nucleus is preferred to be at a pressure that is not greater than the pressure under which the saline solution is injected and is typically on the order of 25-40 psi. While the saline solution has been described as preferably being injected with a vented cannula such as described herein, it should be appreciated that a cannula without a vent, but with a sealing element, could also be used in the practice of the annulus integrity test.

The methods and devices of the present invention are also contemplated for use in performing other open surgical procedures, such as an adjunct to microdiscectomy (AMD) procedure. An AMD procedure is indicated where a total discectomy is not required, or more particularly where only a partial discectomy is necessary to restore normal or near normal function to the affected disc. In a typical case, the affected disc has a herniation or tear in the disc annulus. Access to the intradiscal space is thus available through the tear in the annulus.

Prior to the start of the surgery, the injectable curable polymer constituents are pre-loaded into the mixing assembly, as described above, and left on the sterile instrument table until the appropriate time for injection of the injectable nucleus material. The surgeon uses a traditional open or microdiscectomy technique of preference for access to the disc herniation site. Typically, the patient will be placed on a laminectomy frame in the prone position with the spine flexed to aid intraoperative exposure. The ligamentum flavum and laminar edge are identified. A hemi-laminectomy/medial facetectomy may be performed as necessary, with the aid of lateral fluoroscopy. Exposure of the hernia proceeds in a known manner, taking care to protect the dura and nerve root. The epidural space is explored to ensure that all disc fragments have been identified.

Once the disc herniation has been identified, a determination is made as to whether a further annulotomy is needed for improved access. If so, an annulotomy may be performed as described above. The herniated disc tissue is then removed according to known techniques, such as using pituitary rongeurs and/or curettes. Laminar distraction and/or flexion of the hips can be used to aid in exposure of the hernia site. In addition, distraction of the affected disc may be desired to improve the stability of the disc. This distraction may be accomplished using any of the techniques described above. If sufficient disc tissue has been removed around the herniation site, a distraction balloon may be used, provided that the balloon is removed once the desired distraction has been achieved.

The balloon distraction may also be supplemented in a two stage distraction technique described as follows. After a total or partial nucleotomy has been performed, in the first stage, a distraction balloon is inserted into the intradiscal space. The balloon is then inflated to gain distraction of the anterior column of the disc space. In the second stage, a secondary distraction instrument is introduced to act on any posterior bony structures at the particular intervertebral level in accordance with known surgical techniques. The secondary instrument is used to obtain distraction of the posterior column at an appropriate amount decided by the surgeon. The nature and amount of this second stage distraction may increase the overall amount of distraction of the total space, change the lordotic angle at the intervertebral level or cause no appreciable increase in the overall distraction of the space.

Once the appropriate amount and type of secondary distraction has been obtained, the first stage distraction balloon is removed, while the secondary instrument remains in place to prevent any loss of distraction that may occur. With the distraction balloon removed, the injectable nucleus may be injected as described above. After suitable distraction has been achieved, a saline solution as described above with respect to the DDD procedure may be injected through a vented cannula assembly into the intradiscal space to check the integrity of the annulus and to determine that there are no other leakage paths, as well as to estimate the volume of the intradiscal space to be filled. While this annulus integrity test is described as being conducted after distraction, it may also be done after removal of nucleus and prior to distraction.

When the nuclear cavity has been prepared, the surgeon mixes the injectable nucleus constituents, as described above, to prepare the injectable nucleus material for injection. An injection cannula (which is not required to be a vented and sealed cannula) is introduced through the opening in the annulus until the cannula tip reaches the far side of the cavity. As the injectable nucleus material is injected, the cannula is preferably angled side-to-side and gradually withdrawn toward the annulus to ensure a complete fill of the space. When the injectable nucleus material is detected at the inner border of the annulus opening, the injection is stopped and the cannula is removed from the site. It is contemplated that the injectable nucleus material will be injected under pressure, typically on the order of 25-40 psi, to ensure complete fill of the cavity.

Figure 1:
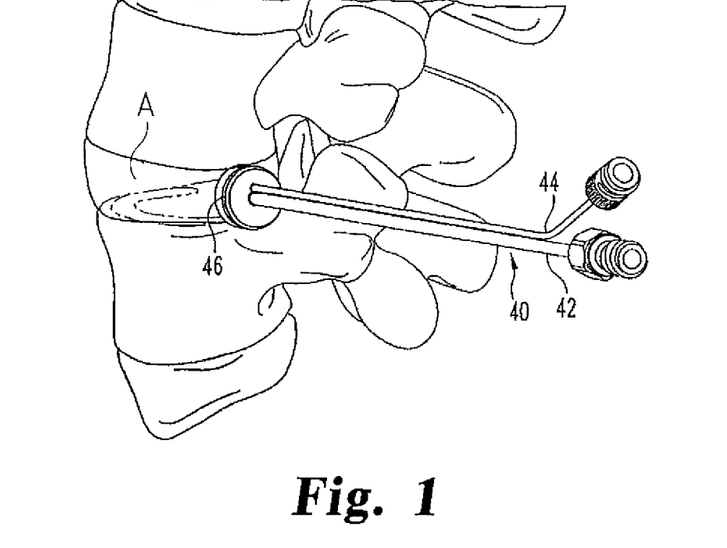
FIG. 1 is an enlarged pictorial view of an injection cannula assembly for introduction of a biomaterial into a disc space.
Figure 2:
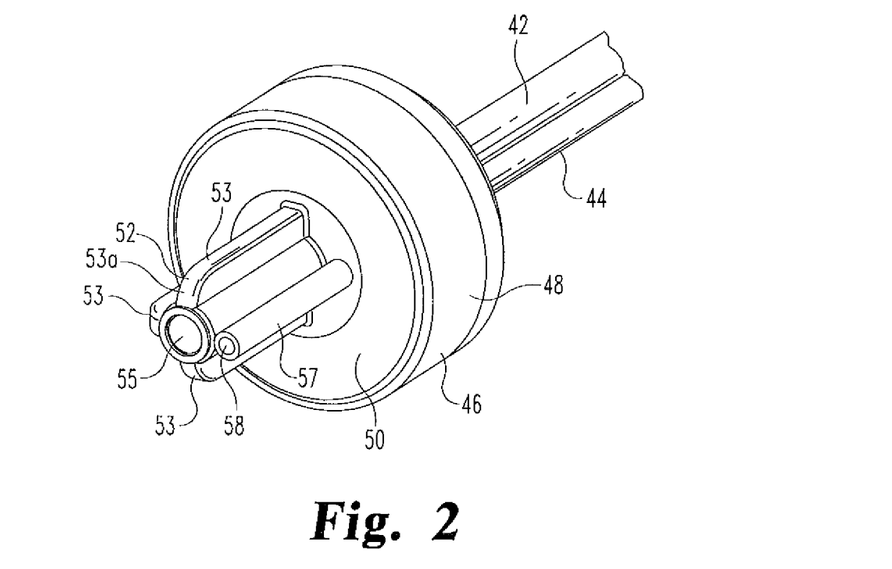
FIG. 2 is a front perspective enlarged view of one form of injection cannula for use in the assembly shown in FIG. 1.
Figure 3:
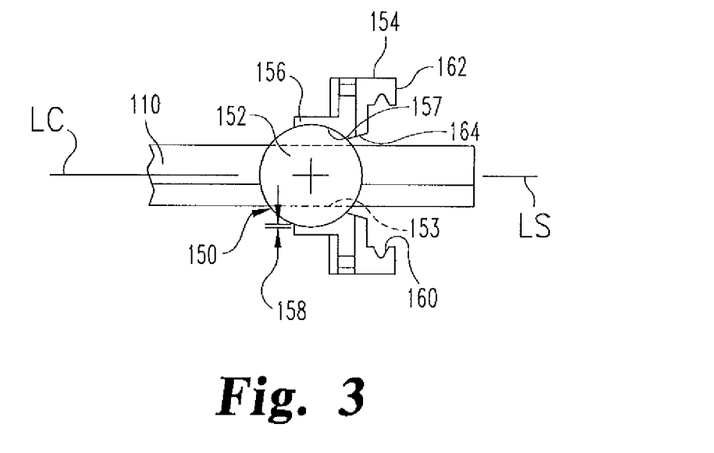
FIG. 3 depicts an articulating seal configured for passage of an injection cannula therethrough to inject a biomaterial into the disc space.

The vented cannula assembly 40 shown in FIGS. 1 and 2, and described above, provides a generally fixed orientation of the cannula 42 relative to the seal 46. In order to maintain a proper seal around the annulotomy, it is important with this assembly 40 that the cannula be aligned substantially perpendicular to the annulus A to avoid unseating one side of the seal In other words, with the seal assembly 40, if the cannula 42 is canted at an angle to the annulus, there is a risk that the seal 46 will pivot with the cannula and unseat from around the annulotomy. The present invention avoids this potential risk by providing an articulating modular seal assembly 150, as shown in FIG. 3, that permits a predetermined range of angulation between the cannula and the seal, and therefore between the cannula and the disc annulus A. In one embodiment, the seal assembly 150 includes a substantially spherical ball 152 that is affixed to an injection needle or cannula 110.

In one embodiment, the ball 152 is formed of a bearing material, such as 304 stainless steel, and is suitably affixed in sealed engagement to the injection cannula 110. The ball defines a bore 153 through which the injection cannula 110 is inserted and preferably fixed in position, such as by welding or press-fit engagement.

Figure 3A:
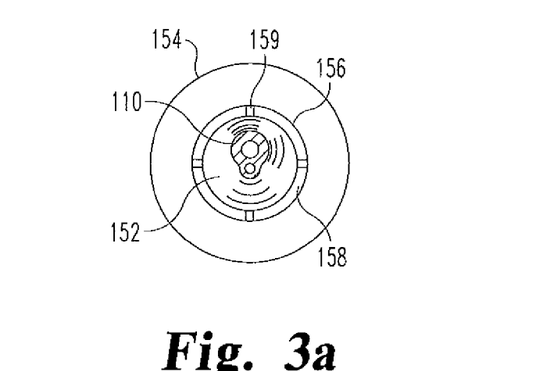
FIG. 3a is an end partial cross-section view of the articulating seal and injection cannula shown in FIG. 3.

In this embodiment, the modular seal assembly 150 includes seal body 154 with a collar 156 configured for bearing contact with the ball 152, and preferably configured to at least partially capture the ball. The collar 156 may thus include a spherical cavity 157 that terminates in an upper lip 158 that is configured to capture the ball within the cavity. The cap 156 and/or the upper lip 158 may be provided with slits 159, as shown in FIG. 3a, that separate as the ball is pressed past the lip into the cavity.

The seal body 154 may be configured to compress as the seal is pressed against he annulus, to thereby improve the seal around the opening. Thus, the body may include an interior feature 160 that permits some deflection or compression of the sealing face 162 when the seal is pressed into the annulus.

The interface between the injection cannula 110, the ball 152 and the cavity 157 is configured to limit the spherical angle of articulation of the injection cannula relative to the seal 150 and disc annulus A. In one embodiment, the seal body 154 defines a conical surface 164 at the opening of the spherical cavity 157. This conical surface provides for a limited degree of angular play before the cannula 110 contacts the surface 164. In a specific embodiment, this "play" is at a spherical angle of about 20°. Thus, the cannula may be oriented with its longitudinal axis LC collinear with the longitudinal axis LS of the seal or the two axes may be angularly offset up to 20° at any point around the circumference of the ball 152. When the seal assembly 150 is engaged to a disc annulus, this capability means that the seal body 154 may remain fully sealed against the annulus while the cannula 152 may be swiveled through the full range of the spherical angle as necessary during the fluid treatment. This range of movement allows the surgeon to manipulate the injection cannula from outside the disc annulus to negotiate the anatomy at the surgical site and allow unfettered access to the injection cannula during the procedure.

In certain modular designs, the seal may incorporate self-anchoring features—i.e., features that temporarily anchor the seal to the disc annulus in a fluid-tight connection. One such seal is the seal 170 shown in FIG. 4. This seal 170 includes a conical body 172 that is adapted to be pressed into the prepared opening through the disc annulus, as might arise in an AMD procedure. Threads 174 are provided on the conical body for threaded engagement within the annulus to anchor the seal as well as the injection cannula to the disc. The seal 170 defines a bore 176 to receive an injection cannula, such as the cannula catheter 42 shown in FIG. 1. In this embodiment, the angular orientation of the injection cannula relative to the seal is generally fixed—i.e., the seal 170 does not permit articulation of the injection cannula passing therethrough. In use, the cannula is introduced through the opening in the annulus until the threads 174 contact. The seal 170 may then be manually rotated to engage the opening and advance the seal farther into the annulus.

Figure 4:
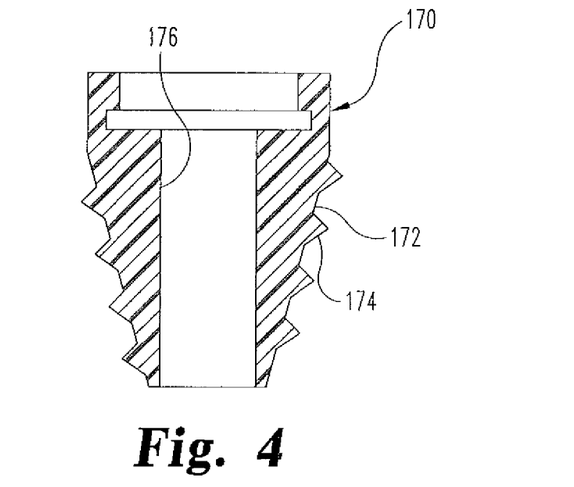
FIG. 4 is a drawing of a self-anchoring seal configured for passage of an injection cannula therethrough to inject a biomaterial into the disc space.
Figure 5:
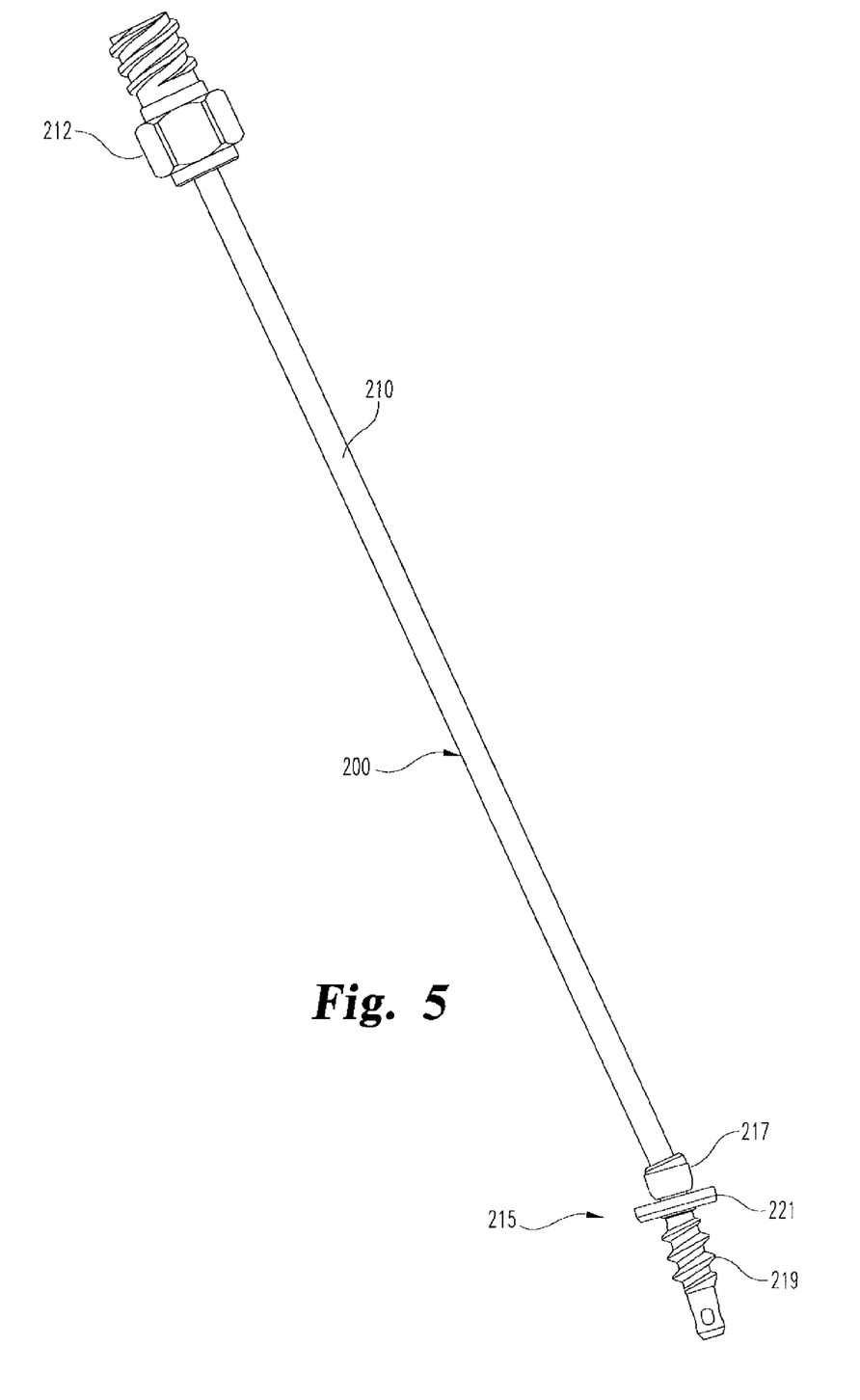
FIG. 5 is a side view of an articulating threaded cannula assembly for introduction of a biomaterial into a disc space according to one embodiment of the invention.
Figure 6:
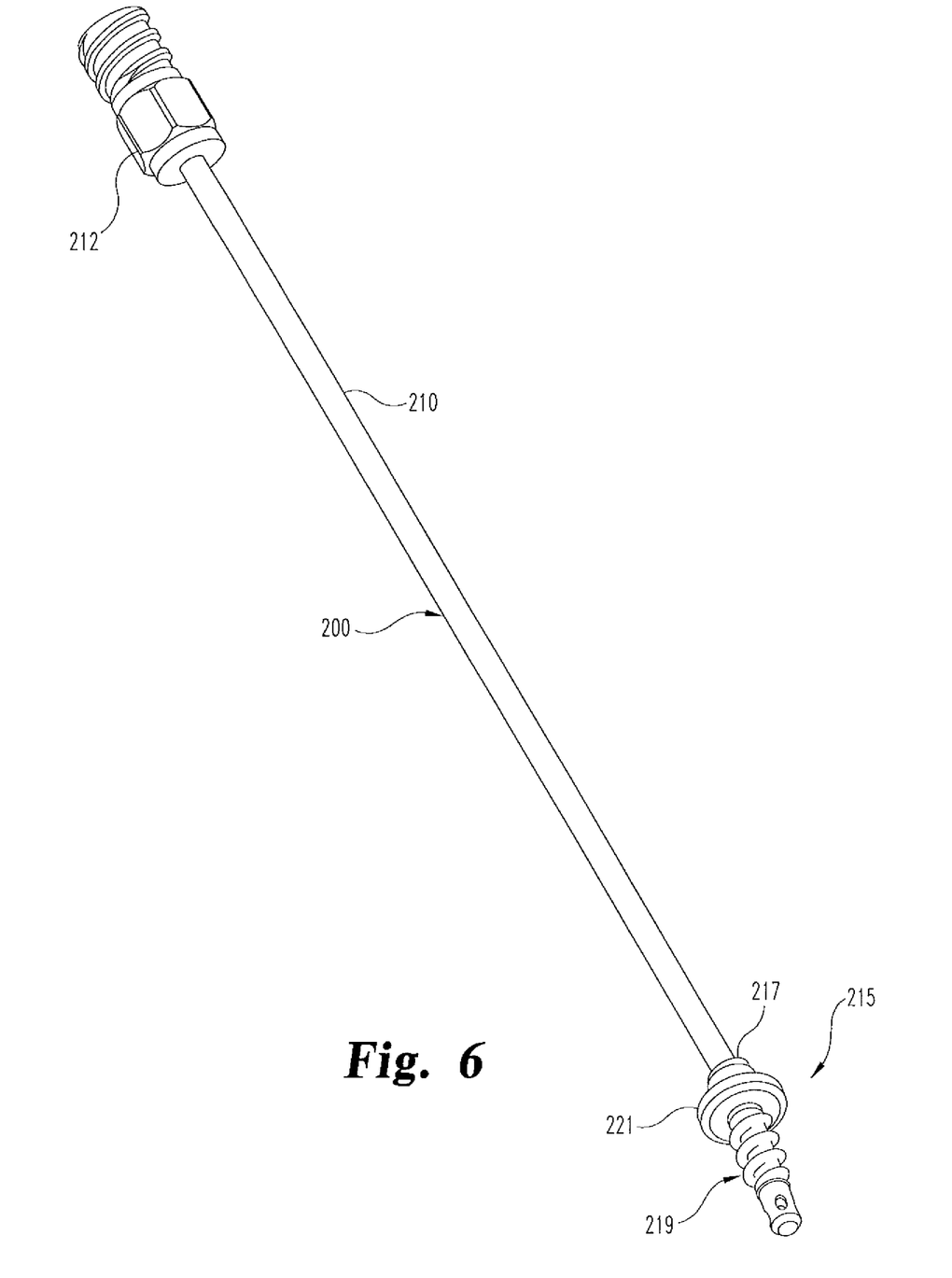
FIG. 6 is a perspective view of the articulating threaded cannula assembly shown in FIG. 5.

Each of the modular injection cannula assemblies illustrated in FIGS. 1-4 provide for sealed engagement with the disc annulus to permit pressurized injection of a biomaterial into the disc space in a DDD or AMD procedure. The modular seal 150 shown in FIGS. 3 and 3a permits limited angulation or articulation of the injection cannula. The seal 170 of FIG. 4 provides a feature for anchoring the assemblies to the disc annulus.

Figure 7:
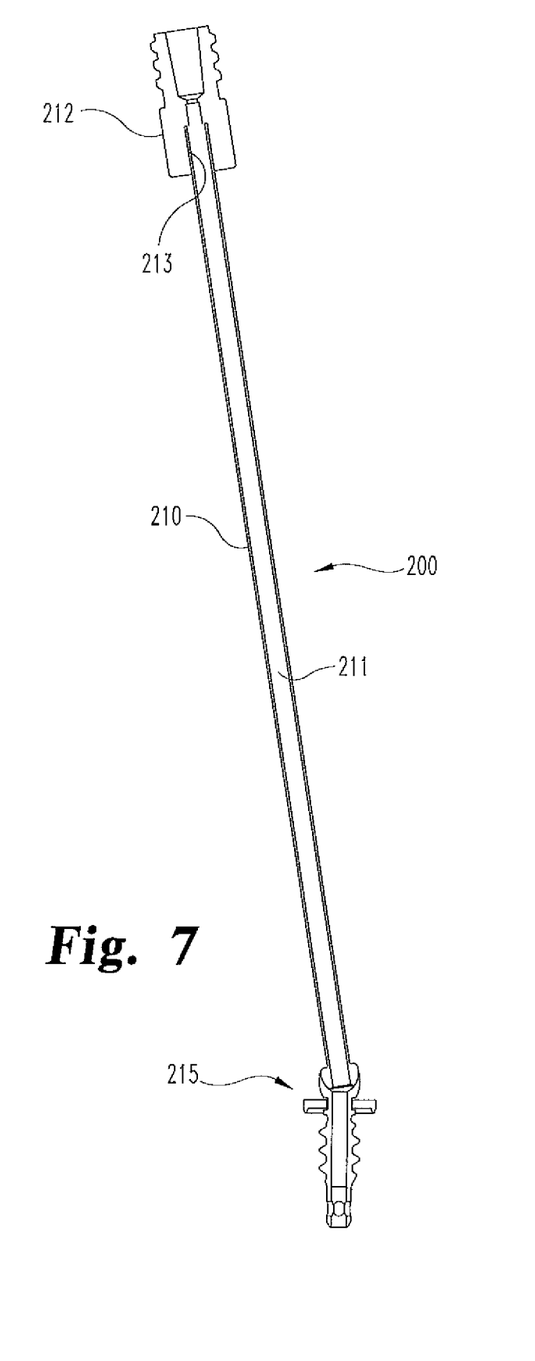
FIG. 7 is a cross-sectional view of the articulating threaded cannula assembly shown in FIG. 5.

In accordance with a further embodiment of the present invention, an injection cannula assembly 200 is provided that combines the articulation and anchoring features of the modular seals 150 and 170. Thus, as shown in FIGS. 5-8, the cannula assembly 200 is configured to achieve a sealed engagement to the disc annulus A while permitting full articulation between the injection cannula and the sealing features. Thus, the assembly 200 includes a cannula 210 with a proximal end fitting 212 that has a length sized so that the fitting 212 is accessible outside the patient while the seal assembly 215 at the opposite or distal working end is engaged to the disc annulus. The seal assembly 215 includes an articulating joint 217, an anchor body 219 and a seal 221. As seen in FIG. 7, the cannula 210 defines a passageway 211 for introduction of a biomaterial into the disc space. The fitting 212 defines a bore 213 for receiving the proximal end of the cannula 210, preferably in sealed fixation. The fitting 212 may be configured to engage a fluid container, such as a hypodermic syringe S, as illustrated in FIG. 9. Thus, in a preferred embodiment, the fitting 212 is configured with a Luer end.

Figure 8:
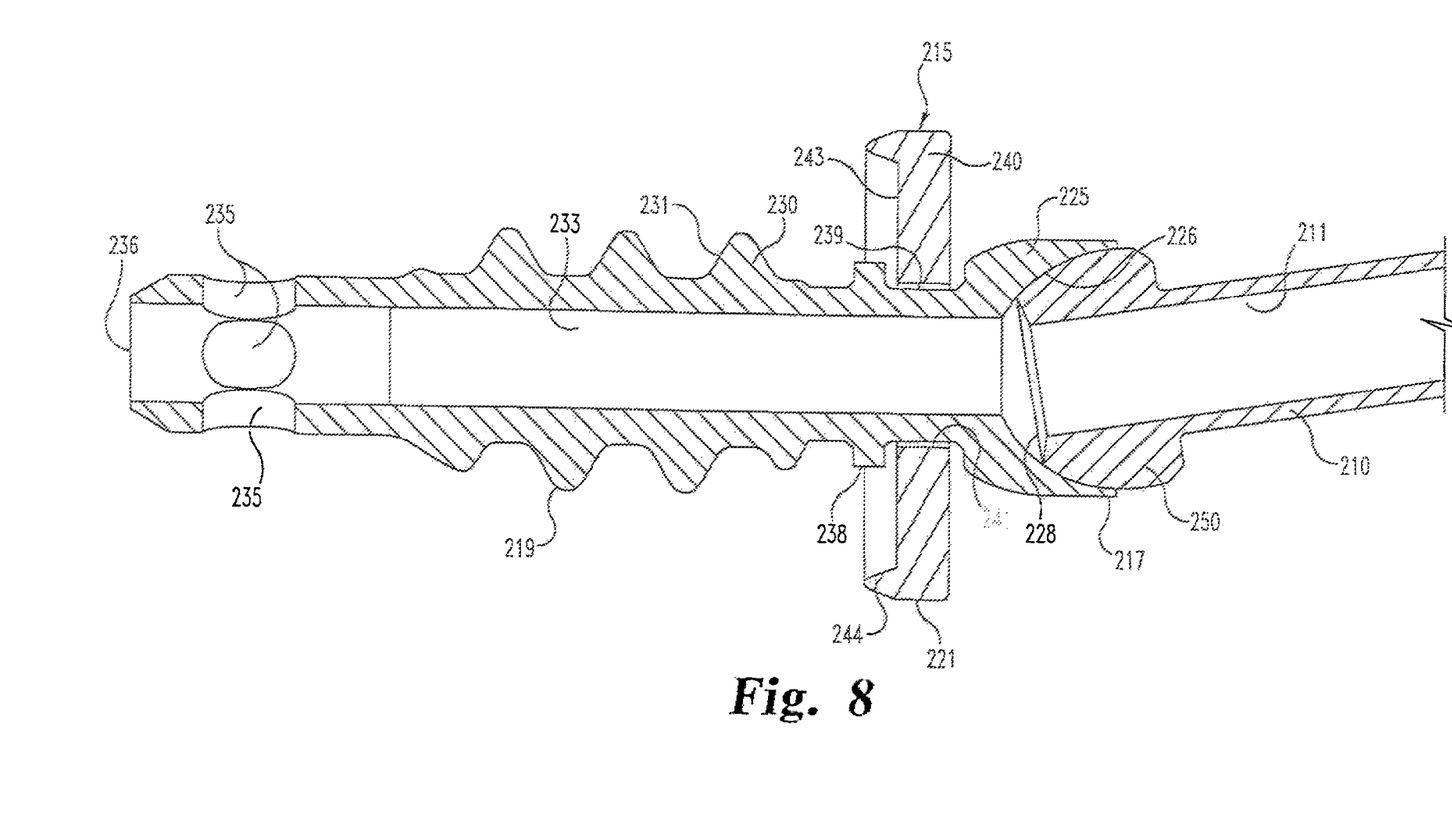
FIG. 8 is an enlarged cross-sectional view of the articulating threaded cannula assembly shown in FIG. 5.
Figure 9:
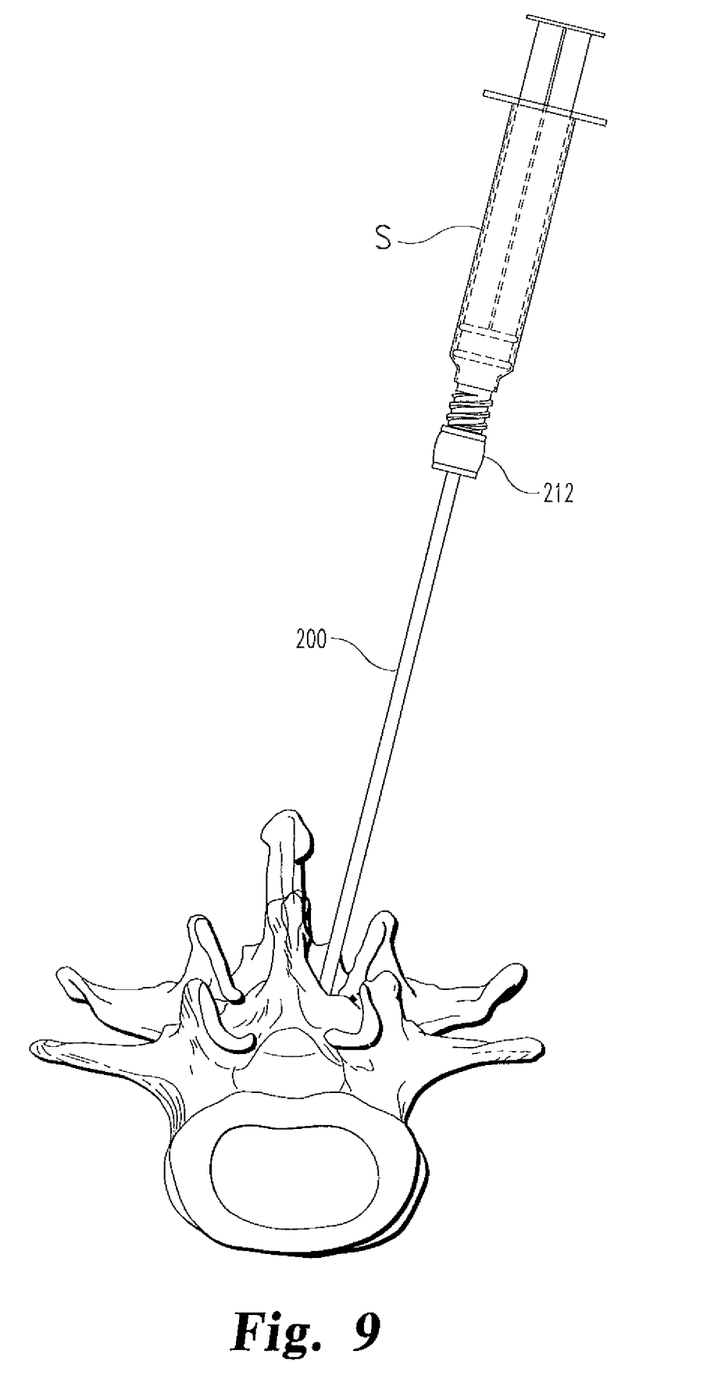
FIG. 9 is a superior view of a vertebral segment with the articulating threaded cannula assembly shown in FIG. 5 engaged with the intervertebral disc, with an injection syringe mounted thereto.

Details of the seal assembly 215 are shown in FIG. 8. The anchor body 219 includes a head 225 that defines a generally spherical cavity 226 forming part of the articulating joint 217. The distal end 250 of the cannula 210 is configured to be received in a sliding, articulating fit within the cavity 226. The cavity 226 opens into a bore 233 that is defined through the elongated tip 230 of the anchor body 219. The tip 230 includes external threads 231 that are adapted to be threaded into an opening in the disc annulus. The end of the tip 230 defines side openings 235 and end opening 236 in communication with the bore 233 for discharge of the biomaterial into the disc space. The tip 230 thus has a length from the head 225 to the end opening 236 that is sufficient to at least traverse the thickness of the disc annulus. The length of the tip may be established to position the discharge openings 235, 236 at a predetermined depth within the disc space.

The elongated tip 230 includes a flange 238 offset from the base of the head 225 to form an annular recess 239 therebetween. The seal 221 is disposed within this recess 239. Thus, the seal 221 includes a body 240 defining a central opening 241 for receiving the elongated tip 230 of the anchor body 219. The central opening 241 is preferably sized so that the anchor body 219 can rotate relative to the seal 221 as the tip 230 is threaded into the disc annulus. Furthermore, the diameter of the central opening is smaller than the head 225 so the head can be brought to bear against the seal to maintain pressure between the seal body 240 and the disc annulus. The body 240 has a thickness at the opening 241 that is less than the width of the annular recess 239.

The seal body 240 preferably defines a cavity 243 formed by a circumferential rim 244. In use, the rim 244 defines a sealing surface that contacts the disc annulus to form a generally fluid-tight seal. The cavity 243 allows the seal 221 to flex under pressure from the head 225 sufficiently to maintain a fluid-tight sealed engagement between the rim 244 and the disc annulus.

The seal 221 is formed of a suitable resilient material, such as a silicone material. The seal material is preferably sufficiently resilient and elastic so that the tip 230 of the anchor body 219 can be pushed through the opening 241 in the seal until the seal springs into position within the annular recess 239 of the anchor body. Alternatively, the seal may be formed by over molding the seal directly onto the annular recess 239.

With the seal in the position shown in FIG. 8, the anchor body 219 may be pushed into an opening, whether prepared or existing, in the disc annulus until the threads 231 encounter the annulus. At this point, the anchor body 219 may be rotated so that the threads 231 engage the annulus. In one aspect, this rotation may be accomplished by interaction with the cannula 210 and rotation of the cannula from outside the patient's body. In this approach, the distal end 250 of the cannula may be configured in a manner that engages the anchor body sufficiently to remotely impart rotation to the anchor body 219. This configuration may entail a friction interface between the opposing surfaces of the cavity 226 and the distal end 250. Alternatively, the distal end 250 may define a ratchet feature that engages the lip 227 of the spherical cavity 226 when the cannula is pulled slightly. Once the anchor body has been fully threaded into the annulus, the cannula can be pushed toward the tip 230 to disengage the ratchet feature and permit fully angulation of the distal end 250 within the cavity 226.

Rotation of the tip 230 advances the seal assembly 215 toward the disc until the seal 221 contacts the annulus. When the assembly is advanced far enough into the disc annulus, the head 225 of the anchor body 219 will bear against the seal 221, thereby sealing the central opening 241 in the seal. The anchor body 219 is advanced far enough into the disc annulus so that the rim 244 of the seal 221 is in sealing contact around the entire perimeter of the rim. It should be appreciated that the planar configuration of the seal 221 may be circular or elliptical to achieve a complete fluid-tight seal with the disc annulus. Other planar configurations are contemplated depending upon the nature of the annular surface to be engaged by the seal and the configuration of the opening in the annulus.

The seal assembly 215 further incorporates an articulating joint 217 in which one portion of the joint is defined by the spherical cavity 226 in the head 225 of the anchor body 219. The mating portion of the joint includes a generally spherical bulb 251 at the distal end 250 of the cannula 210. The bulb 251 may be integrally formed with the body of the cannula or may be a separate component fixed to the distal end of the cannula. As can be appreciated from FIG. 8, the spherical bulb 251 is truncated where the passageway 211 intersects the end of the cannula. A circumferential relief 228 is preferably formed at that intersection with the passageway 211 so that the flowable biomaterial may always flow from the cannula passageway 211 into the passageway 233 of the anchor body 219, regardless of the angular orientation of the bulb 251 relative to the cavity 226.

In one embodiment, the interface between the spherical bulb 251 and the head 225 of the anchor body 219 may be a snap-fit or press-fit engagement. In this embodiment, the lip 227 of the cavity has a diameter that is slightly less than the diameter of the cavity itself. The spherical bulb 251 of the cannula distal end has a spherical diameter that approximates the spherical diameter of the cavity so that the reduced diameter lip 227 will hold the bulb within the cavity. It is contemplated that the articulating joint 217 may be pre-assembled—i.e., the cannula 210 is engaged to the seal assembly 215 prior to introduction of the anchor body 219 into the disc annulus. Alternatively, the seal assembly may be initially detached from the cannula as the anchor body 219 is introduced into the annulus. Once the seal has been established, the spherical end 250 may be engaged with the cavity 226 of the anchor body to complete the articulating joint 217.

The anchor body 219 is preferably formed of a biocompatible material that is sufficiently strong to be threaded into the disc annulus. Thus, the body may be formed of stainless steel or other similar metal. The body may also be molded form a strong polymer, particularly for single use, disposable applications.

In the illustrated embodiment, the articulating joint 217 is in the form of a ball and socket joint. Other joint configurations are contemplated that permit wide angle relative movement between the cannula 210 and the seal assembly 215 while also maintaining a relatively fluid-tight seal. The "tightness" of the joint—i.e., the closeness of the fit of the running components—may be determined by the viscosity of the fluid being injected into the disc space. In other words, flowable biomaterials in the nature of a gel or other high viscosity material may not require as tight a seal within the articulating joint as a low viscosity, highly flowable material might. For low viscosity biomaterials, the articulating joint may require additional sealing characteristics, such as seal rings disposed between the spherical bulb 251 and the cavity 226.

It can be appreciated that the articulating joint 217 is configured to permit relative articulation between the cannula 210 and the seal assembly 215 in a spherical angle, limited only by contact between the cannula 210 itself and the head 225 of the anchor body. In a specific embodiment, the cannula can pivot through a spherical angle of about 40° or more. Moreover, the articulating joint may be configured to allow the cannula to rotate or swivel a full 360° about its axis while the spherical bulb 251 is disposed within the spherical cavity 226 of the joint.

It is contemplated in certain embodiments that the bore 233 of the anchor body 219 may be configured to receive a driving tool, such as by providing a hex configured proximal portion. The shaft of the driving tool may be sized to extend through the length of the cannula 210 into engagement with the bore 233. Alternatively, if the articulating joint is formed by attachment of the cannula after the seal assembly 215 has been engaged to the disc annulus, then the driving tool may be appropriately sized.

With respect to the articulating joint, it is contemplated in certain embodiments that the joint 217 is configured to impart rotation from the cannula 210 to the anchor body 219 to engage the threads 231 within the disc annulus. In the illustrated embodiment of FIG. 8, this rotation may be transferred through frictional engagement between the spherical bulb 251 and the spherical cavity 226. Interdigitating surface features may be added to the ball and socket interface to enhance the ability to transfer rotation from the cannula to the anchor body without disturbing the articulation capability of the joint. Alternatively, a coupling member (not shown) may be extended through the passageway 211 of the cannula to engage the bore 233 of the anchor body 219 to impart rotation to the anchor body.

Figure 10:
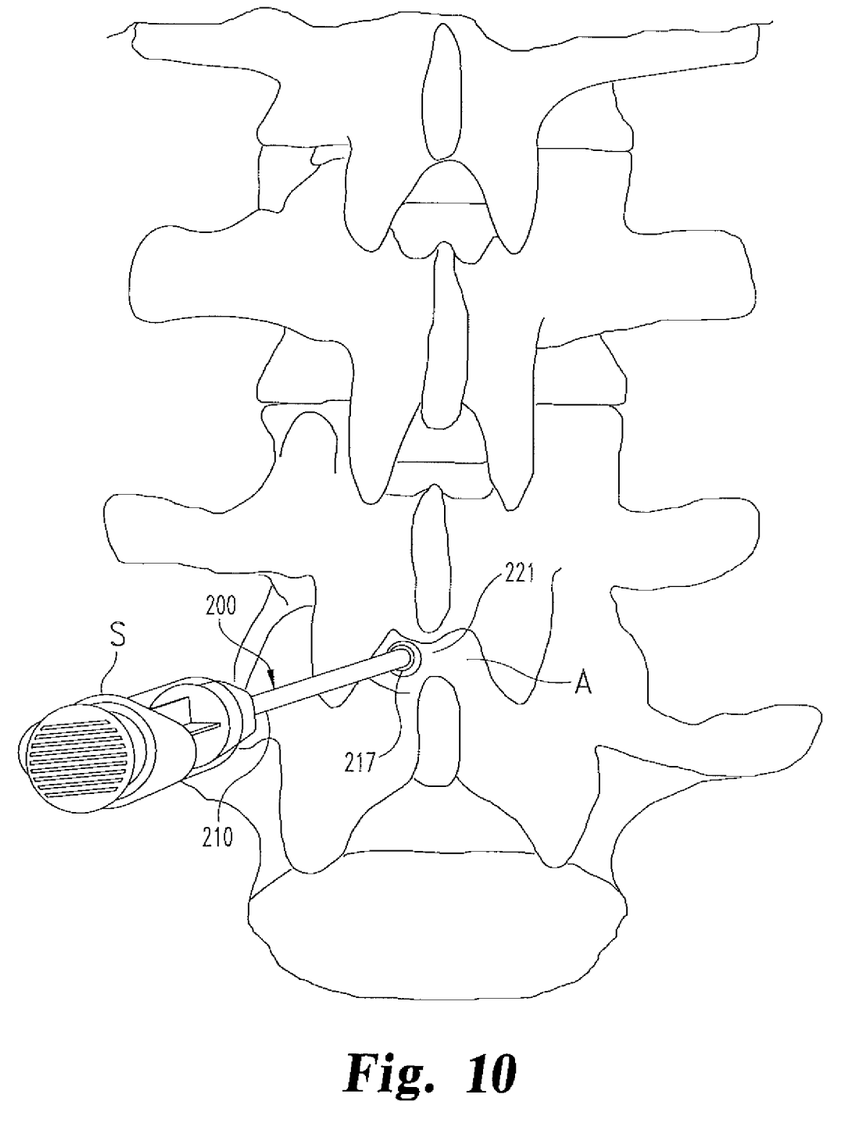
FIG. 10 is an anterior view of the articulating threaded cannula assembly engaged to the intervertebral disc as depicted in FIG. 9.

Use of the injection cannula assembly 200 of the present invention is depicted in FIGS. 9-10. The fitting 212 is shown engaged to a standard hypodermic syringe S that has been previously filled with a curable biomaterial, as discussed above. The plunger of the syringe S allows the surgeon to apply manual pressure to inject the biomaterial into the disc space. As seen in FIG. 10, the articulating feature of the cannula assembly 200 allows the cannula 210 to be manipulated as necessary to negotiate access to the intervertebral disc annulus A between the adjacent vertebral bodies.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. An assembly for sealably injecting a fluent material into an intradiscal space accessed through an opening in the annulus of a spinal disc, comprising:
   a cannula having a passageway for injecting the fluent material therethrough into the intradiscal space, said cannula having a proximal end and a distal end;
   a seal on said cannula comprising a collar and a seal body, said seal body defining a central opening and having a solid sealing surface, said seal body being disposed more distally on said cannula than said collar and being configured with an interior depression to be compressible under manual pressure between said collar and an outer surface of said annulus adjacent to and externally of the opening as said sealing surface is pressed against said annulus, said central opening of said seal body being sized for passage of said cannula therethrough, with said distal end of said cannula being disposed exteriorly of one side of said seal body and said proximal end being disposed exteriorly of a side opposite to the one side of said seal body; and
   an articulating joint being configured to permit relative articulation between said seal and each of said distal and proximal ends of said cannula when said cannula extends through said central opening, wherein said articulating joint includes a ball and socket joint, wherein said socket is a generally spherical cavity defined in said seal; and wherein said ball is a generally spherical ball sized to articulate within said cavity and said ball defines a bore sized to receive said cannula therethrough.

2. The assembly according to claim 1, wherein said cannula is affixed to said ball within said bore.

3. The assembly according to claim 2, wherein said cannula is affixed to said ball so that said distal end of said cannula extends into the intradiscal space when said sealing surface of said seal engages the disc annulus.

4. The assembly according to claim 1, wherein said collar defines said cavity.

5. The assembly according to claim 4, wherein said collar further includes a lip sized to retain said ball within said cavity.

6. An assembly for sealably injecting a fluent material into an intradiscal space accessed through an opening in the annulus of a spinal disc, comprising:
   a cannula having a passageway for injecting the fluent material therethrough into the intradiscal space, said cannula terminating in a proximal end and a distal end, wherein the distal end includes an enlarged tip portion;
   a seal having a solid sealing surface for sealing engagement with the outer surface of the disc annulus and defining a central opening; and
   an anchor element extending through said central opening of said seal, said anchor element including an elongated body disposed exteriorly distally of said seal and sized for sealing engagement within the opening in the disc annulus and defining a bore in fluid communication with said passageway of said cannula for injecting the fluent material therethrough into the intradiscal space, said anchor element having a head disposed exteriorly proximally of said seal and defining an internal cavity, the enlarged tip portion of said cannula being received in said internal cavity in a sliding articulating joint, wherein the enlarged tip portion in not permitted to move distally of the internal cavity.

7. The assembly according to claim 6, wherein:
   said anchor element defines an annular recess at a proximal end thereof between said elongated body and said portion disposed exteriorly proximally of said seal; and
   said central opening in said seal is sized to receive therein said anchor element at the location of said annular recess.

8. The assembly according to claim 7, wherein said annular recess has a width and said seal has a thickness at said central opening that is sized to permit relative sliding of said seal along said width.

9. The assembly according to claim 6, wherein said elongated body defines at a distal end thereof external threads for threading the opening in the disc annulus while said anchor element is extending through said central opening of said seal.

10. The assembly according to claim 6, wherein:
said cavity defined in said head of said anchor element comprises a spherical surface; and
said cannula is sized so that said proximal end thereof is accessible outside the patient's body when the distal end is received in said cavity.

11. An assembly for sealably injecting a fluent material into an intradiscal space accessed through an opening in the annulus of a spinal disc, comprising:
a cannula having a passageway for injecting the fluent material therethrough into the intradiscal space, said cannula having a proximal end and a distal end, wherein the distal end of the cannula includes an enlarged tip portion;
a seal on said cannula having a solid sealing surface for sealing engagement with the outer surface of the disc annulus and defining a central opening, said seal including a compressible seal body having a circumferential rim defining therewithin a cavity facing said distal end of said cannula, said cavity allowing said seal to flex under pressure applied on said seal body toward said sealing surface, said rim defining said sealing surface capable of forming a fluid-tight seal between said rim and said disc annulus; and
an articulating joint defined between said central opening of said seal and said cannula configured to permit relative articulation therebetween, wherein said enlarged tip portion of said cannula is articulatingly supported by said seal exteriorly proximally of said seal such that the enlarged tip portion is not permitted to move distally of a proximal surface of the seal.

* * * * *